(12) United States Patent
Cannon

(10) Patent No.: US 8,976,017 B1
(45) Date of Patent: Mar. 10, 2015

(54) METHOD FOR INSPECTING DOWN HOLE DRILLING SYSTEMS FOR FLAWS USING ULTRASONICS

(75) Inventor: Shawn Paul Cannon, Willis, TX (US)

(73) Assignee: Osnel de la Cruz Rodriguez, Porter, TX (US)

( * ) Notice: Subject to any disclaimer, the term of this patent is extended or adjusted under 35 U.S.C. 154(b) by 909 days.

(21) Appl. No.: 13/085,050

(22) Filed: Apr. 12, 2011

Related U.S. Application Data

(60) Provisional application No. 61/323,741, filed on Apr. 13, 2010.

(51) Int. Cl.
*G08B 23/00* (2006.01)
*G08B 21/00* (2006.01)

(52) U.S. Cl.
USPC ........... 340/514; 340/518; 340/519; 340/679; 340/680; 367/81; 367/82

(58) Field of Classification Search
None
See application file for complete search history.

(56) References Cited

U.S. PATENT DOCUMENTS

| | | | |
|---|---|---|---|
| RE29,734 E * | 8/1978 | Manning | 367/83 |
| 5,078,954 A | 1/1992 | Smith et al. | |
| 5,159,838 A | 11/1992 | Lynnworth | |
| 5,283,768 A * | 2/1994 | Rorden | 367/83 |
| 5,686,668 A * | 11/1997 | McLean | 73/622 |
| 5,969,255 A * | 10/1999 | McLean | 73/622 |
| 6,332,361 B1 * | 12/2001 | Yamada et al. | 73/627 |
| 6,719,069 B2 * | 4/2004 | Alft et al. | 175/24 |
| 8,214,161 B2 * | 7/2012 | Girndt | 702/39 |
| 2010/0329081 A1 * | 12/2010 | Sullivan et al. | 367/120 |

* cited by examiner

*Primary Examiner* — Julie Lieu
(74) *Attorney, Agent, or Firm* — Buskop Law Group, PC; Wendy Buskop

(57) ABSTRACT

A method for inspecting down hole drilling systems for identifying indications of flaws in material. The method can include removing particulate, disposing a wave coupling medium on an area of interest, attaching a probe to a sound carrying wedge, engaging the sound carrying wedge over the wave coupling medium, transmitting inspection signals to the area of interest, manipulating the probe to produce detection signals, transmitting the detection signals to a data storage, presenting the detection signals and a known reference level to a user, and comparing the detection signals to the known reference level to determine if the detection signals are within a standard deviation of the known reference level. The method can include adapting a sound carrying wedge to form-fittingly couple to an area of interest of a down hole drilling system.

20 Claims, 6 Drawing Sheets

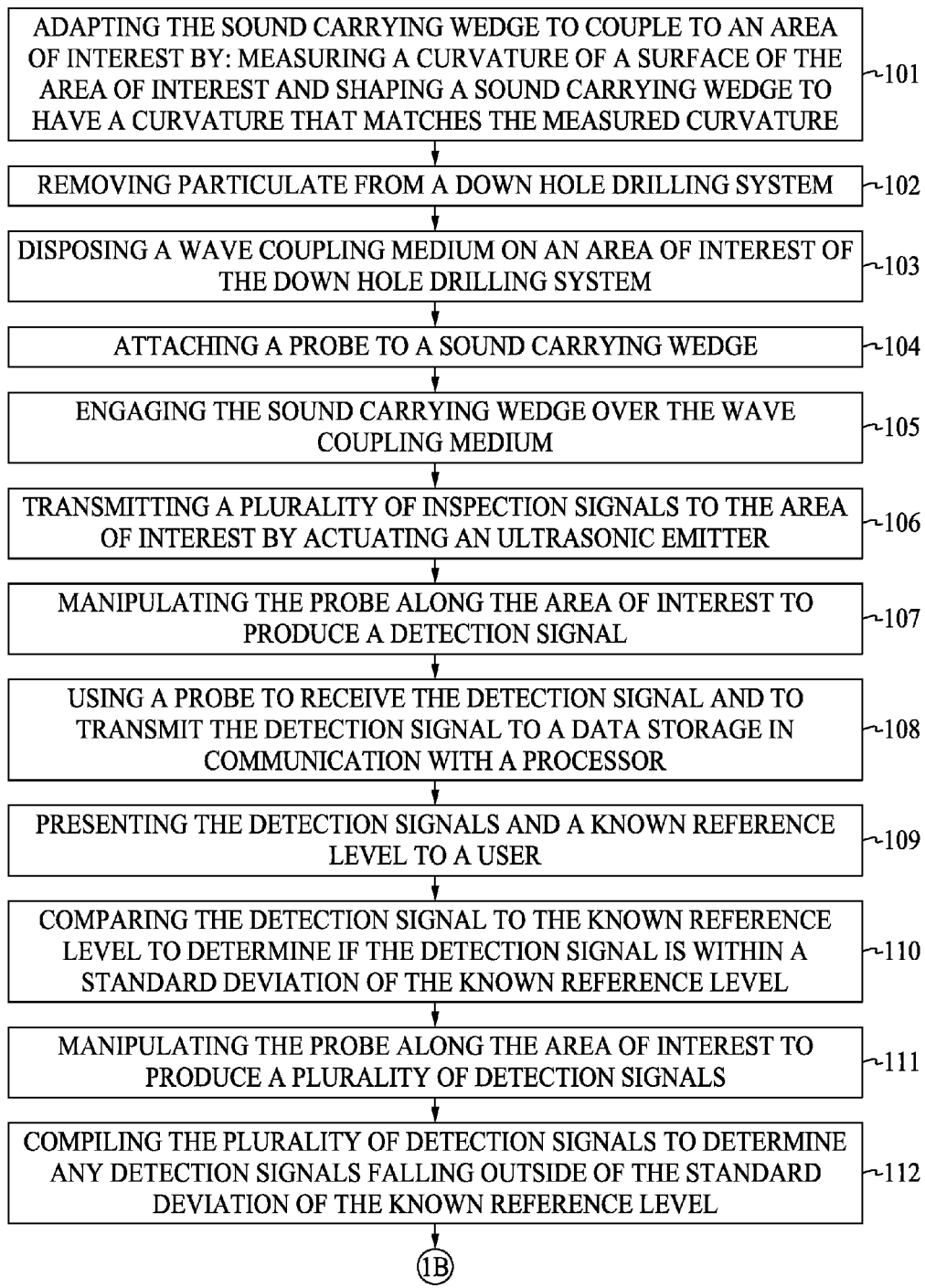

FIGURE 3A

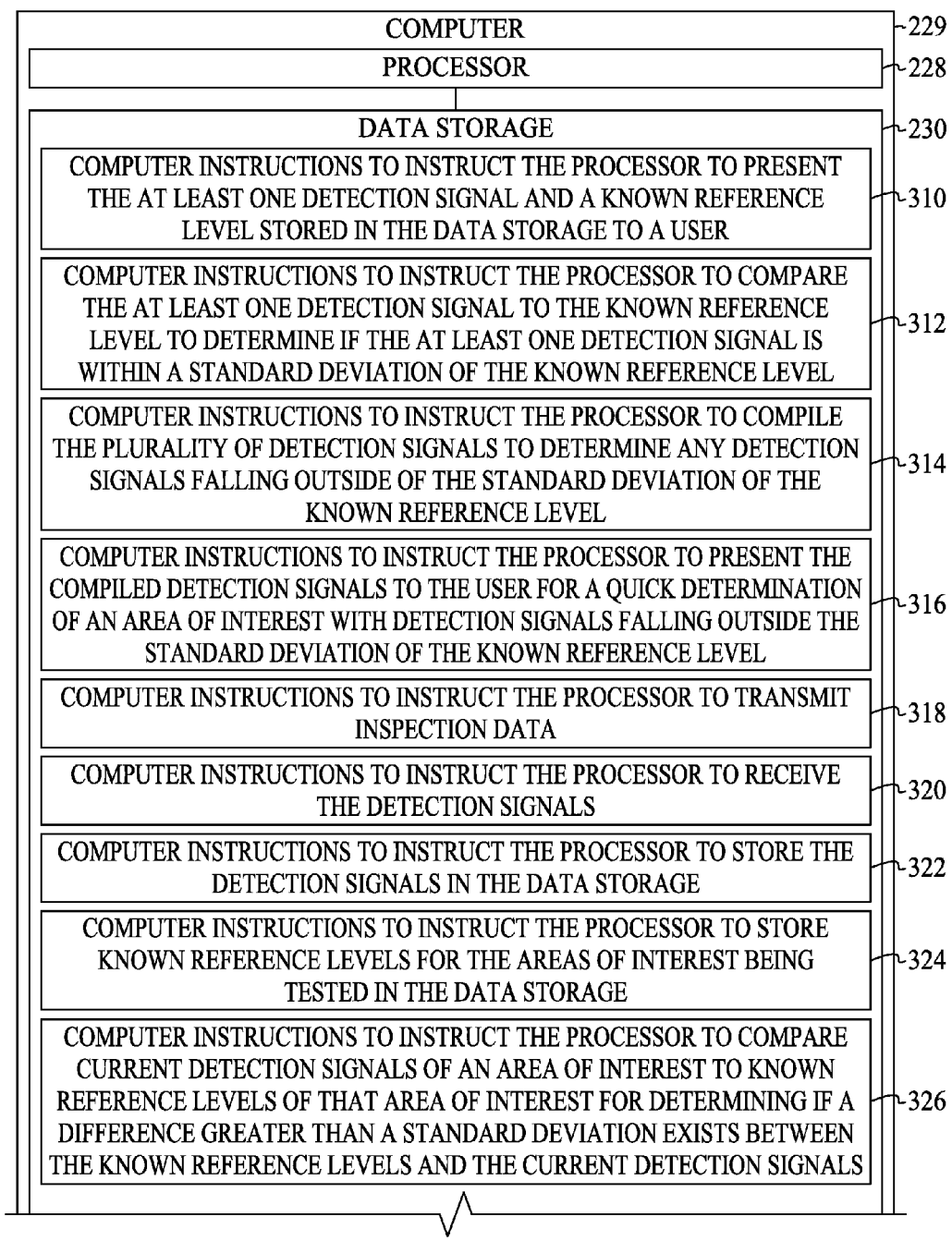

| | |
|---|---|
| COMPUTER | 229 |
| PROCESSOR | 228 |
| DATA STORAGE | 230 |
| COMPUTER INSTRUCTIONS TO INSTRUCT THE PROCESSOR TO PRESENT THE AT LEAST ONE DETECTION SIGNAL AND A KNOWN REFERENCE LEVEL STORED IN THE DATA STORAGE TO A USER | 310 |
| COMPUTER INSTRUCTIONS TO INSTRUCT THE PROCESSOR TO COMPARE THE AT LEAST ONE DETECTION SIGNAL TO THE KNOWN REFERENCE LEVEL TO DETERMINE IF THE AT LEAST ONE DETECTION SIGNAL IS WITHIN A STANDARD DEVIATION OF THE KNOWN REFERENCE LEVEL | 312 |
| COMPUTER INSTRUCTIONS TO INSTRUCT THE PROCESSOR TO COMPILE THE PLURALITY OF DETECTION SIGNALS TO DETERMINE ANY DETECTION SIGNALS FALLING OUTSIDE OF THE STANDARD DEVIATION OF THE KNOWN REFERENCE LEVEL | 314 |
| COMPUTER INSTRUCTIONS TO INSTRUCT THE PROCESSOR TO PRESENT THE COMPILED DETECTION SIGNALS TO THE USER FOR A QUICK DETERMINATION OF AN AREA OF INTEREST WITH DETECTION SIGNALS FALLING OUTSIDE THE STANDARD DEVIATION OF THE KNOWN REFERENCE LEVEL | 316 |
| COMPUTER INSTRUCTIONS TO INSTRUCT THE PROCESSOR TO TRANSMIT INSPECTION DATA | 318 |
| COMPUTER INSTRUCTIONS TO INSTRUCT THE PROCESSOR TO RECEIVE THE DETECTION SIGNALS | 320 |
| COMPUTER INSTRUCTIONS TO INSTRUCT THE PROCESSOR TO STORE THE DETECTION SIGNALS IN THE DATA STORAGE | 322 |
| COMPUTER INSTRUCTIONS TO INSTRUCT THE PROCESSOR TO STORE KNOWN REFERENCE LEVELS FOR THE AREAS OF INTEREST BEING TESTED IN THE DATA STORAGE | 324 |
| COMPUTER INSTRUCTIONS TO INSTRUCT THE PROCESSOR TO COMPARE CURRENT DETECTION SIGNALS OF AN AREA OF INTEREST TO KNOWN REFERENCE LEVELS OF THAT AREA OF INTEREST FOR DETERMINING IF A DIFFERENCE GREATER THAN A STANDARD DEVIATION EXISTS BETWEEN THE KNOWN REFERENCE LEVELS AND THE CURRENT DETECTION SIGNALS | 326 |

METHOD FOR INSPECTING DOWN HOLE DRILLING SYSTEMS FOR FLAWS USING ULTRASONICS

CROSS REFERENCE TO RELATED APPLICATION

The present application claims the priority to and the benefit of U.S. Provisional Patent Application Ser. No. 61/323,741 filed on Apr. 13, 2010, entitled "METHOD FOR INSPECTING DOWN HOLE DRILLING SYSTEMS FOR FLAWS USING ULTRASONCIS". This reference is hereby incorporated in its entirety.

FIELD

The present embodiments generally relate to a method for inspecting down hole drilling systems for flaws using ultrasonic waves.

BACKGROUND

A need exists for a method for inspecting down hole drilling systems that is capable of providing safe, efficient, and accurate inspection data, thereby producing a safer environment for inspectors utilizing the method and for workers utilizing the down hole drilling systems.

A need exists for a method for inspecting down hole drilling systems using sound carrying wedges that are adapted to form-fittingly couple to portions of the down hole drilling systems.

A need exists for a method for inspecting down hole drilling systems using sound carrying wedges that can provide ultrasonic signals at a plurality of predetermined inspection signal angles, thereby reducing the need to scan a large area with ultrasonic waves during inspection.

A need exists for a method for inspecting using sound carrying wedges that can fit within small surface areas of down hole drilling systems, thereby providing a method for accurately inspecting small surface area portions of down hole drilling systems.

A need exists for a method for inspecting using a phased array probe that can use multiple elements to steer, focus and scan ultrasonic inspection signals with a single transducer assembly.

A further need exists for a method for inspecting down hole drilling systems using a probe adapted to provide a plurality of inspection signals in a single signal transmission, thereby more thoroughly inspecting the down hole systems.

The present embodiments meet these needs.

BRIEF DESCRIPTION OF THE DRAWINGS

The detailed description will be better understood in conjunction with the accompanying drawings as follows:

FIGS. 1A-1B is a flow chart of an embodiment of the method.

FIGS. 3A-3B is an embodiment of a computer that can be used to practice one or more embodiments of the method.

Figure 1B:
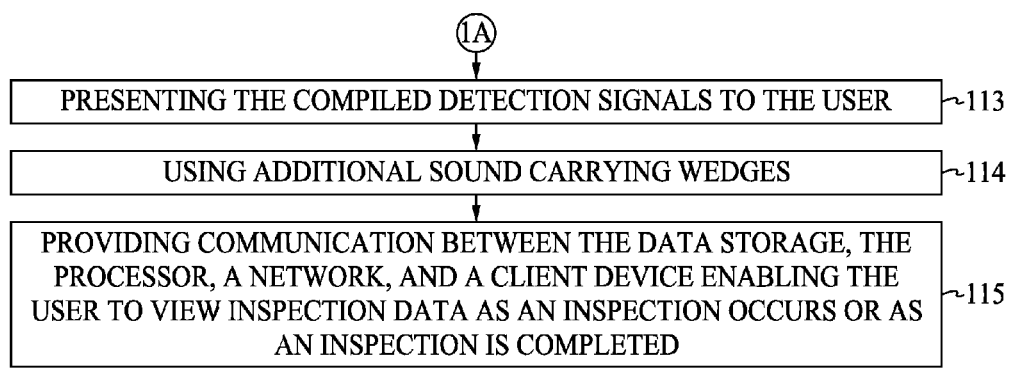

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

The present embodiments relate to a method for inspecting down hole drilling systems for internal and external flaws such as fractures, cracks, hairline cracks, rust, degradation, corrosion, build-up of residue, discontinuities, back walls, other material boundaries and other types of flaws found in the inherent, processing and servicing of the down hole drilling system. The method can be used to inspect welds and to profile remaining wall thickness in a corrosion survey. Embodiments of the method can be used to inspect for a variety of flaws and is not limited to the illustrative examples provided herein.

Down hole drilling systems, as the term is herein used, refers to drilling motors, drilling motor components, drilling tools, drilling tool components, mud motor bottom hole assemblies, tubulars, cylindrical components of down hole tools and drilling systems, ball bearings, housings, threaded areas of the down hole drilling system, transition areas of the down hole drilling system, gap subs, and any other component of a down hole drilling system.

Embodiments of the method can be used for providing a safe environment for inspectors and for workers by ensuring that the down hole drilling system is free of flaws since flawed down hole drilling systems can lead to dangerous operating conditions. When a down hole drilling system is found to be flawed by use of the method, the down hole drilling system can be removed, replaced, and/or repaired.

Embodiments of the method can be used for providing an efficient way of inspecting down hole drilling systems partly because the method can collect inspection data at a single small area rather than having to collect inspection data by scanning a larger area at multiple points.

Embodiments of the method can provide more accurate inspection data by using multiple angles of inspection signals able to create a sectoral scan display rather than an inspection signal with a single angle only capable of producing an A-Scan display.

One or more embodiments can include removing particulate from the down hole drilling system.

The particulate can be mud, dirt, rocks, sand, debris, any foreign material on the surface that may obstruct the movement or sensitivity of the inspection scan, and other forms of particulate.

The particulate can be removed using a mechanical grinder, a liquid such as water or a chemical, or combinations thereof. A hose or a pressure washer can be used to remove the particulate. The particulate can be removed from the exterior and interior of the down hole drilling system.

The method can include disposing a wave coupling medium, also herein referred to as a wave focusing fluid, on an area of interest of the down hole drilling system. The wave coupling medium can be disposed by spreading, smearing, daubing, or brushing the wave focusing fluid onto the area of interest.

The wave coupling medium can provide a coupling between a sound carrying device or sound carrying wedge and the area of interest of the down hole drilling system.

The wave coupling medium can be an ultrasound or ultrasonic conductive gel or liquid such as water, couplant, or another medium capable of receiving and transmitting ultrasonic waves. Ultrasonic conductive liquids, gels, and other mediums usable in the method are well known to those skilled in the art.

The area of interest of the down hole drilling system can include an area that a user chooses to inspect for flaws.

One or more embodiments of the method can include engaging a probe onto a sound carrying device, such as a sound carrying wedge. The probe can be attached to the sound carrying device by nuts and bolts, screws, or another fastening means. The probe can be in electrical communication with a power source.

The probe can include or can support an ultrasonic emitter. In one or more embodiments the ultrasonic emitter can be or can include at least one ultrasonic transducer that can convert energy into ultrasound.

In one or more embodiments, the ultrasonic emitter can include at least one element or a plurality of elements, such as a crystal or a plurality of crystals. The elements or crystals can be piezoelectric crystals, which can be piezoelectric transducers that can convert electrical energy into sound.

For example, the ultrasonic emitter can have a plurality of crystals which can each have the property of changing size when a voltage is applied to the crystals. The crystals can be caused to oscillate by applying an alternating current (AC) across the crystals. The oscillation of the plurality of crystals can be at high frequencies and each of the plurality of crystals can therefore produce an inspection signal in the form of a high frequency sound wave such that the plurality of crystals can produce and provide a plurality of inspection signals.

The probe can be actuable, such as by providing a current to the probe, such that the probe is actuated to provide a plurality of inspection signals. In one or more embodiments the probe can produce from about sixteen to about sixty four inspection signals in the form of sound waves. The plurality of inspection signals can be provided simultaneously and/or sequentially.

One or more embodiments can include using a phased array probe as the probe. A phased array probe usable in the method can include a transducer assembly with from about sixteen individual elements to about two hundred fifty-six individual elements that can each be pulsed or actuated separately. Each individual element can be arranged in a linear array, an annular array, a circular array, or another shape.

Transducer frequencies usable in the method can include frequencies ranging from about one MHz to about twenty-five MHz. The method can include use of other frequencies.

The method can include using a phased array probe that includes a computer that can actuate the phased array probe. The computer can include a data storage, a processor, a display, or combinations thereof.

The inspection signals can reflect or echo from the area of interest as detection signals. The method can include using a phased array probe that can receive or detect the returning or echoing detection signals from the area of interest.

The method can include digitizing the detection signals and plotting the echo information in various formats, which can be performed using the computer and computer instructions stored therein.

The method can include using a phased array probe that can sweep an ultrasonic inspection signal through a range of refracted angles, along a linear path, or can dynamically focus the ultrasonic inspection signals at a number of different depths, thus increasing both flexibility and capability in the method.

In operation, the phased array probe can be used to vary a length of time between a series of outgoing ultrasonic inspection signals in such a way that each individual ultrasonic wave generated by each individual element can combine with each other to add or cancel energy, thereby effectively steering and shaping the ultrasonic inspection signal. For example, the method can include pulsing or actuating each individual probe element at a slightly different time. The individual elements can be pulsed in groups from about four to about thirty-two in order to improve effective sensitivity by increasing aperture, which can reduce unwanted ultrasonic inspection signal spreading and enable sharper focusing of the ultrasonic inspection signal.

The method can include using software stored in the data storage, such as a focal law calculator software program that can establish or predetermine specific delay times for actuating each group of elements in order to generate a desired ultrasonic inspection signal shape, forming a programmed pulsing sequence.

The focal law calculator software program can take into account the probe and sound carrying wedge characteristics as well as the geometry and acoustical properties of the down hole drilling system.

The programmed pulsing sequence can be selected by an operating software of the phased array probe. The phased array probe can then be used to emit a number of individual ultrasonic wave fronts into the area of interest. The individual ultrasonic wave fronts can in-turn combine constructively and destructively into a single primary ultrasonic inspection signal that can travel through the down hole drilling system and can reflect off of flaws and back to the phased array probe for detection as a detection signal.

The method can include manipulating the phased array probe or dynamically steering the ultrasonic inspection signals through various angles, focal distances, and focal spot sizes in such a way that a single phased array probe can be used to examine the down hole drilling system across a range of different perspectives.

Ultrasonic inspection signal steering, also referred to as sectorial scanning, can be used for mapping components at appropriate angles, thereby simplifying the inspection of components with complex geometries.

The method can include using a phased array probe with a small footprint, thereby allowing a user to sweep the ultrasonic inspection signals without moving the phased array probe. The method can therefore aide in inspection of components wherein there is limited spatial access for mechanical scanning.

The ability to test welds with multiple angles from a single probe using the method increases the probability of detection of anomalies.

The method can include using electronic focusing of the ultrasonic inspection signals, permitting for optimization of the ultrasonic inspection signal beam shape and size at an expected flaw location, thus further optimizing the probability of detection of flaws or other material features.

The method can include focusing the ultrasonic inspection signals at multiple depths, improving the ability for sizing of critical flaws for volumetric inspections. Focusing of the ultrasonic inspection signals can significantly improve signal-to-noise ratio in challenging applications, and electronic scanning across many groups of elements allows for C-Scan images to be produced very rapidly.

An A-scan is a simple RF waveform presentation showing the time and amplitude of an ultrasonic inspection signal, as provided by ultrasonic flaw probes and waveform display thickness gages. An A-scan waveform represents the reflections from one sound beam position in the component being tested. The columnar ultrasonic inspection signal from a common single-element contact transducer intercepts two out of three holes on a calibration reference block and generates two distinct reflections at different times that are proportional to the depth of the holes.

An S-scan, or sectorial scan image represents a two-dimensional cross-sectional view derived from a series of A-scans that have been plotted with respect to time delay and refracted angle. The horizontal axis of the plot of an S-scan corresponds to the width of the area of interest, and the vertical axis corresponds to a depth of the area of interest.

In one or more embodiments, the ultrasonic inspection signals can be swept through a series of angles to generate an approximately cone-shaped cross-sectional image. By sweeping the ultrasonic inspection signals, the phased array probe can map all three holes from a single position on a calibration reference block.

The ultrasonic inspection signal steering can occur quickly, such that an inspection scan from multiple angles or with multiple focal depths can be performed quickly, such as in a fraction of a second.

The returning detection signals can be received by the various elements or groups of elements of the phased array probe. The detection signals can be time-shifted as necessary to compensate for varying wedge delays and then the detection signals can be summed. The time shifting and summing of the detection signals can be performed using the computer and computer instructions stored therein.

The method can include using a phased array probe that can spatially sort the returning detection signals according to the arrival time and amplitude of each detection signal at each element. The spatial sorting of the detection signals can be performed using the computer and computer instructions stored therein.

The detection signals can be transmitted to the data storage and can be processed by instrument software stored in the data storage. Each returned detection signal represents a reflection from a particular angular component of the ultrasonic inspection signal, a particular point along a linear path, and/or a reflection from a particular focal depth. The detection signals and processed information associated with the detection signals can be displayed in any of several formats, such as on the display of the computer.

In one or more embodiments, the sound carrying device or wedge can be formed of ceramic, rexolite, or another material capable of transmitting sound waves.

The sound carrying device or wedge can be adapted to form-fittingly couple to portions of down hole drilling systems, such as curved portions.

The sound carrying device or wedge can have a bottom surface, which can be a curved contact surface. The curved contact surface can be curved to precisely match a curvature of the area of interest, such that when the curved contact surface is disposed over the area of interest the curved contact surface is in full contact with the area of interest. Such full contact can provide a high transmission rate of inspection signals from the sound carrying device or wedge, through the coupling medium, and into the down hole drilling system by eliminating spatial gaps between the bottom surface of the sound carrying device or wedge and the area of interest.

The sound carrying device or wedge can be adapted to receive the plurality of inspection signals from the probe and to disperse the plurality of inspection signals at a plurality of predetermined inspection signal angles.

The method can include engaging the first sound carrying device or wedge with the probe attached thereto over the wave coupling medium disposed on the area of interest.

The method can include actuating the probe to provide a plurality of inspection signals, as ultrasonic signals, to the sound carrying device or wedge, which can in-turn transmit the plurality of inspection signals to the wave coupling medium. The wave coupling medium can then transmit the plurality of inspection signals to the area of interest.

The plurality of inspection signals can pass into material of the down hole drilling system, each at an angle, and each inspection signal can then reflect back out of the down hole drilling system at an angle.

One or more embodiments can include scanning the area of interest to derive a first inspection signal. Scanning the area of interest can include manipulating the probe along the area of interest while actuating the probe.

The probe can be in communication with a data storage. The probe can transmit detection signals to the data storage. The data storage can be in communication with a processor. The data storage and processor can be standard commercially available data storage and processor.

The method can include using computer instructions stored in the data storage to instruct the processor to receive the detection signals. The method can include using computer instructions stored in the data storage to instruct the processor to store the detection signals in the data storage.

The method can include using computer instructions stored in the data storage to instruct the processor to store known reference levels for the areas of interest being tested in the data storage. Known reference levels can be values for detection signals from previous ultrasonic inspections of the area of interest.

The method can include using computer instructions stored in the data storage to instruct the processor to compare current detection signals of an area of interest to known reference levels of that area of interest for determining if a difference greater than a standard deviation exists between the known reference levels and the current detection signals.

The method can include using computer instructions stored in the data storage to instruct the processor to compile a plurality of inspection signals to determine which inspection signals fall outside a standard deviation of any one of the stored known reference levels.

The method can include using computer instructions stored in the data storage to instruct the processor to present the compiled inspection signals, the detection signals, the known reference levels, or combinations thereof to a user for quick determination of the area of interest with inspection signals falling outside of a standard deviation of the stored known reference levels.

One or more embodiments can include a display in communication with the processor, the data storage, the probe, or combinations thereof. The display can be a television monitor, a computer monitor, an LCD or plasma screen, or any other type of screen usable with the method.

One or more embodiments can include using additional sound carrying devices or wedges. Each sound carrying device or wedge can enable an additional inspection signal to be derived for the area of interest or from another area of interest. Each additional sound carrying device or wedge can be specifically and precisely machined to exactly and precisely match a curvature of at least one area of interest.

In one or more embodiments, the sound carrying devices or wedges can be adapted to provide ultrasonic inspection signals ranging from about zero degrees to about ninety degrees.

In one or more embodiments, the data storage, the processor, the probe, or combinations thereof can be in communication with a network, enabling a user to view inspection data, including detection signals, in real time, continually, or continuously as inspection occurs or as inspections are completed. The network can be a satellite network, a cellular network, the internet, a wireless network, or another network.

The method can include using computer instructions in the data storage to instruct the processor to transmit inspection data. The inspection data can include the compiled inspection signals, the detection signals, the known reference levels, information about the inspector performing the inspection, other inspection related information, or combinations thereof.

One or more embodiments can include a client device in communication with the network for receiving the inspection data and for presenting the inspection data to a user of the client device. The client device can be a computer, a lap top, a tablet, or a mobile phone.

One or more embodiments of the method can include adapting a sound carrying device or wedge to couple to the area of interest by measuring a shape, including a curvature, of a surface of an area of interest. Next, a sound carrying device or wedge that is not adapted to couple to the area of interest can be machined or otherwise cut such that the sound carrying device or wedge has a shape or curvature that precisely matches the shape or curvature of the area of interest.

Turning now to the Figures, FIG. 1A shows a flow chart of an embodiment of the method.

A first step 101 can include adapting the sound carrying wedge to couple to an area of interest by: measuring a curvature of a surface of the area of interest and shaping a sound carrying wedge to have a curvature that matches the measured curvature.

A second step 102 can include removing particulate from a down hole drilling system.

A third step 103 can include disposing a wave coupling medium on an area of interest of the down hole drilling system.

A fourth step 104 can include attaching a probe to a sound carrying wedge.

A fifth step 105 can include engaging the sound carrying wedge over the wave coupling medium.

A sixth step 106 can include transmitting a plurality of inspection signals to the area of interest by actuating an ultrasonic emitter.

A seventh step 107 can include manipulating the probe along the area of interest to produce a detection signal.

An eighth step 108 can include using a probe to receive the detection signal and to transmit the detection signal to a data storage in communication with a processor.

An ninth step 109 can include presenting the detection signals and a known reference level to a user.

The detection signals and the known reference level can be stored in the data storage. The presentation can be done by using computer instructions stored in the data storage to present the detection signal and a known reference level.

A tenth step 110 can include comparing the detection signal to the known reference level to determine if the detection signal is within a standard deviation of the known reference level.

An eleventh step 111 can include manipulating the probe along the area of interest to produce a plurality of detection signals.

A twelfth step 112 can include compiling the plurality of detection signals to determine any detection signals falling outside of the standard deviation of the known reference level.

FIG. 1B is a continuation of FIG. 1A. FIG. 1B depicts a thirteenth step 113, which can include presenting the compiled detection signals to the user.

A fourteenth step 114 can include using additional sound carrying wedges.

A fifteenth step 115 can include providing communication between the data storage, the processor, a network, and a client device enabling the user to view inspection data as an inspection occurs or as an inspection is completed.

Figure 2:
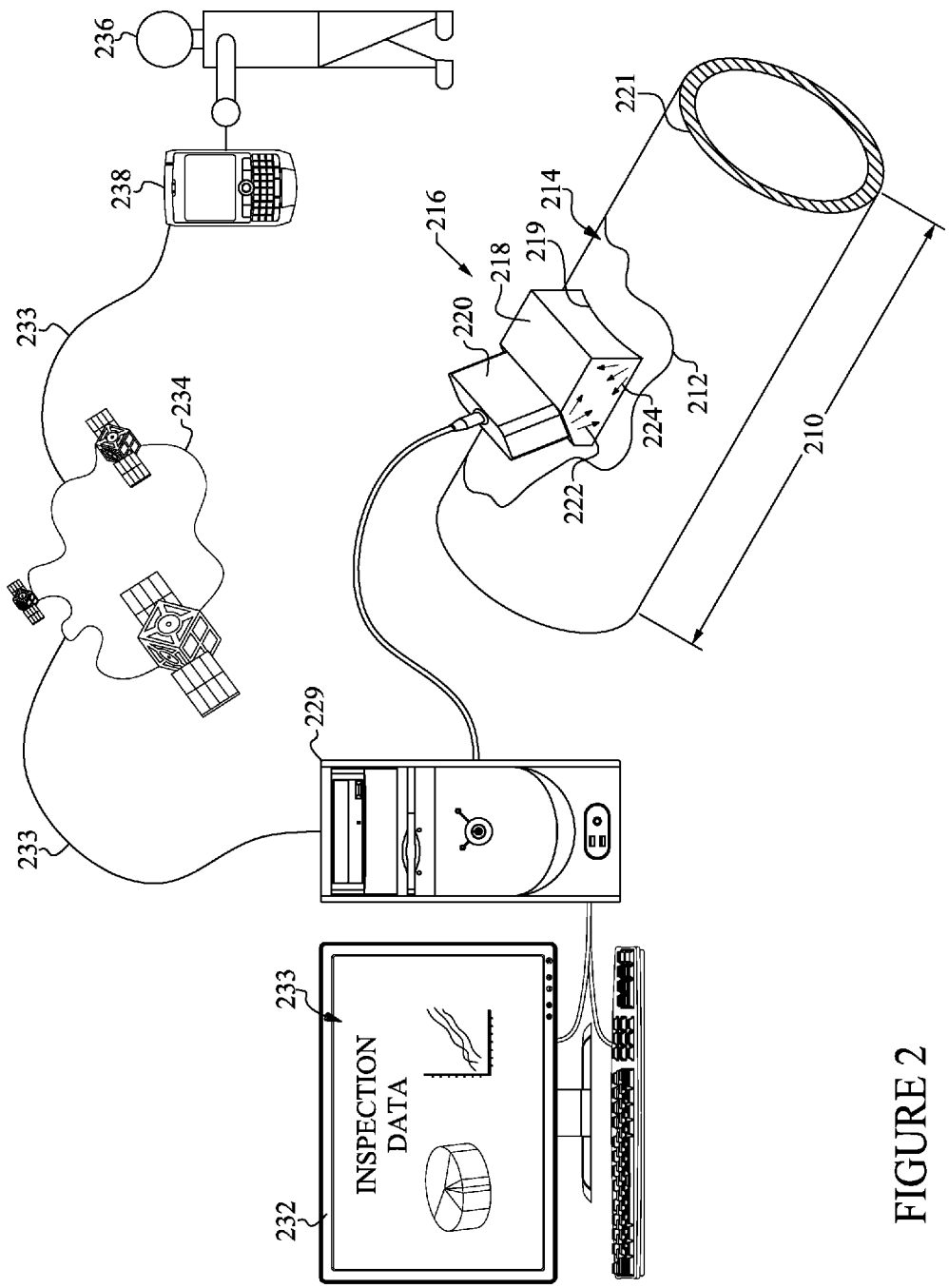
FIG. 2 is an embodiment of a system that can be used to practice one or more embodiments of the method.

FIG. 2 shows an embodiment of a system usable to implement the method.

A portion of a down hole drilling system 210 is depicted. A wave coupling medium 212 is shown disposed on an area of interest 214 of the down hole drilling system.

A probe 216 is shown attached to a sound carrying wedge 218. A curvature 219 of the sound carrying wedge 218 that matches a curvature 221 of the surface of the area of interest 214 is also shown. The probe 216 is shown including an ultrasonic emitter 220.

A plurality of inspection signals 222 are depicted being transmitted into the area of interest 214 at various angles. A plurality of detection signals 224 are shown reflecting from the area of interest 214 at various angles.

The probe 216 is shown receiving the plurality of detection signals 224. The probe 216 can also be in communication with a computer 229.

The computer 229 can be in communication with a display 232 for presentation of inspection data 233.

The computer 229 can be in communication with a network 234. A user 236 is shown with a client device 238 in communication with the network 234 for receiving the inspection data 233 from the computer 229, enabling the user to view the inspection data 233 as an inspection occurs or as an inspection is completed.

FIG. 3A shows an embodiment of the computer 229 including a processor 228 in communication with a data storage 230 with a plurality of computer instructions.

The data storage 230 can include computer instructions 310 to instruct the processor to present the at least one detection signal and a known reference level stored in the data storage to a user.

The data storage 230 can include computer instructions 312 to instruct the processor to compare the at least one detection signal to the known reference level to determine if the at least one detection signal is within a standard deviation of the known reference level.

The data storage 230 can include computer instructions 314 to instruct the processor to compile the plurality of detection signals to determine any detection signals falling outside of the standard deviation of the known reference level.

The data storage 230 can include computer instructions 316 to instruct the processor to present the compiled detection signals to the user for a quick determination of an area of interest with detection signals falling outside the standard deviation of the known reference level.

The data storage 230 can include computer instructions 318 to instruct the processor to transmit inspection data.

The data storage 230 can include computer instructions 320 to instruct the processor to receive the detection signals.

The data storage 230 can include computer instructions 322 to instruct the processor to store the detection signals in the data storage.

The data storage 230 can include computer instructions 324 to instruct the processor to store known reference levels for the areas of interest being tested in the data storage.

The data storage 230 can include computer instructions 326 to instruct the processor to compare current detection signals of an area of interest to known reference levels of that area of interest for determining if a difference greater than a standard deviation exists between the known reference levels and the current detection signals.

Figure 3B:
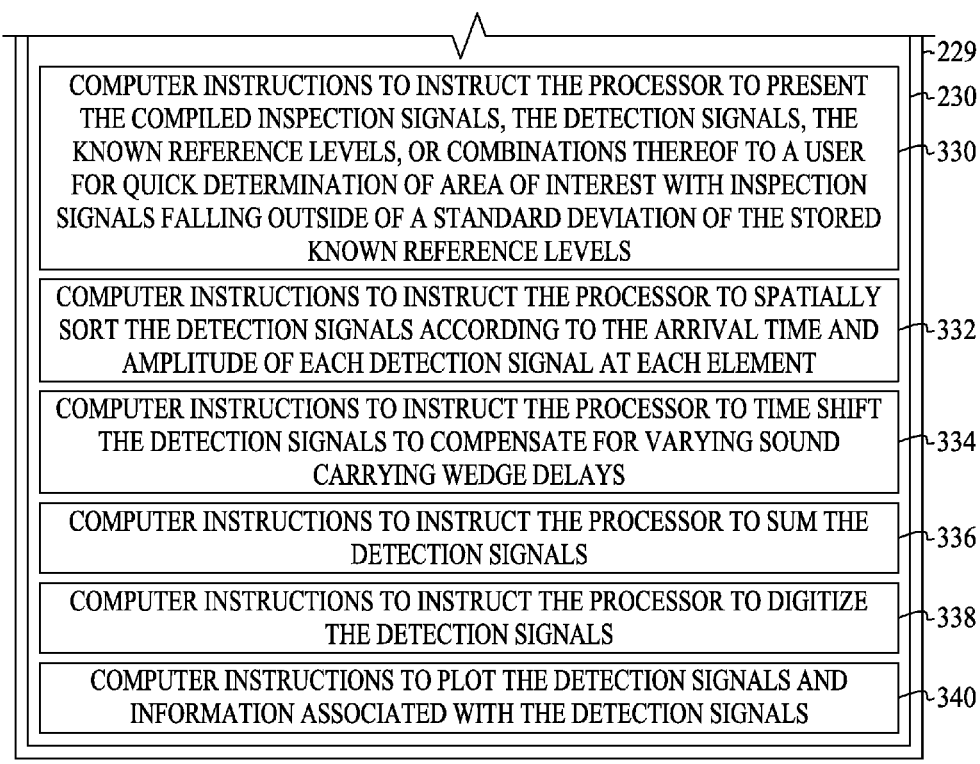

FIG. 3B is a continuation of FIG. 3A. FIG. 3B depicts data storage 230, which can include computer instructions 330 to instruct the processor to present the compiled inspection signals, the detection signals, the known reference levels, or combinations thereof to a user for quick determination of area of interest with inspection signals falling outside of a standard deviation of the stored known reference levels.

The data storage 230 can include computer instructions 332 to instruct the processor to spatially sort the detection signals according to the arrival time and amplitude of each detection signal at each element.

The data storage 230 can include computer instructions 334 to instruct the processor to time shift the detection signals to compensate for varying sound carrying wedge delays.

The data storage 230 can include computer instructions 336 to instruct the processor to sum the detection signals.

The data storage 230 can include computer instructions 338 to instruct the processor to digitize the detection signals.

The data storage 230 can include computer instructions 340 to plot the detection signals and information associated with the detection signals.

Figure 4:
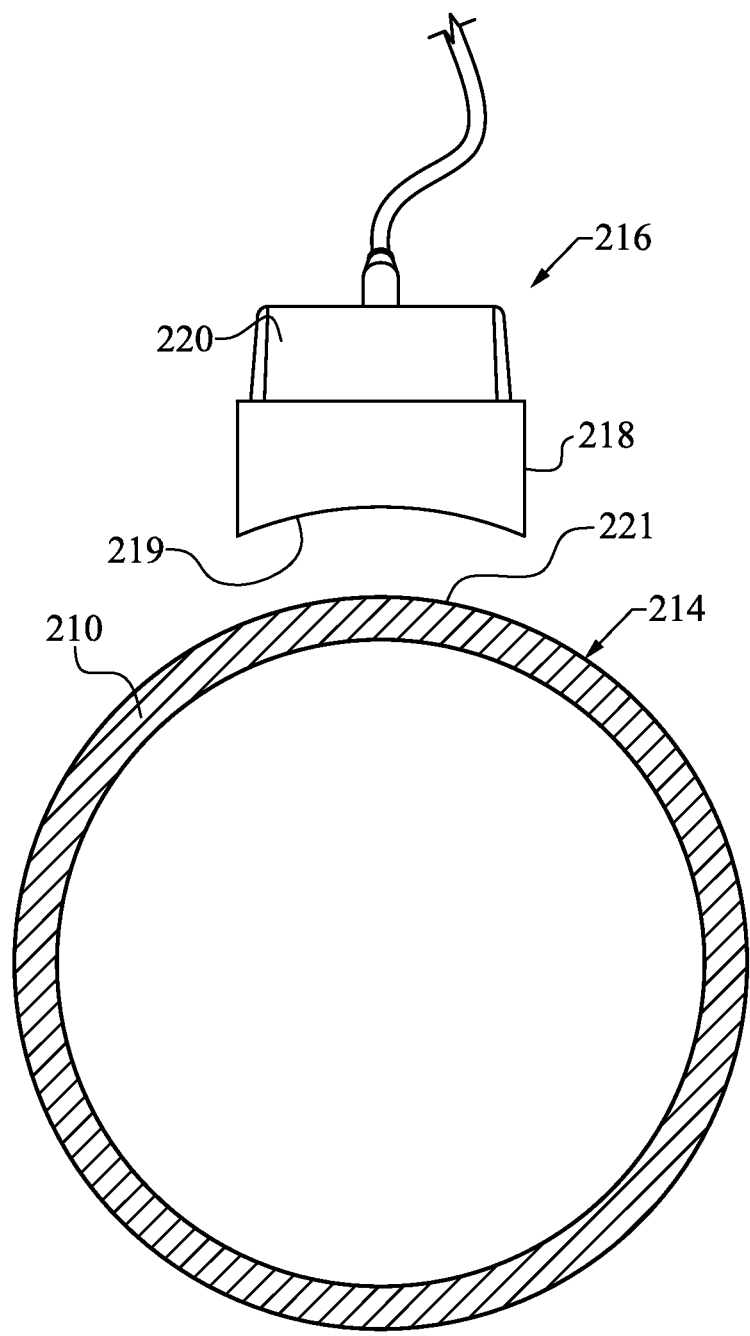
FIG. 4 is an exploded front view of a portion of a down hole drilling system and a sound carrying wedge.

FIG. 4 shows an exploded front view of a sound carrying wedge 218 and a portion of a down hole drilling system 210. The probe 216 is shown including an ultrasonic emitter 220.

A curvature 219 of the sound carrying wedge 218 that matches a curvature 221 of the surface of the area of interest 214 is shown.

The curvature 219 can extend along an entire surface of one side of the sound carrying wedge 218. The curvature 221 can extend along an entire surface of one side of the area of interest 214, such that when curvature 219 is disposed over curvature 221, the two curvatures are in contact. In one or more embodiments the two curvatures can be in full and complete contact with one another.

While these embodiments have been described with emphasis on the embodiments, it should be understood that within the scope of the appended claims, the embodiments might be practiced other than as specifically described herein.

What is claimed is:

1. A method for inspecting down hole drilling systems for identifying indications of flaws in material, the method comprising:
    a. removing particulate from a down hole drilling system;
    b. disposing a wave coupling medium on an area of interest of the down hole drilling system, wherein the wave coupling medium is capable of transmitting ultrasonic waves;
    c. attaching a probe to a sound carrying wedge, wherein the probe comprises an ultrasonic emitter array comprising a plurality of ultrasonic emitter elements configured to be independently actuated, wherein each ultrasonic emitter element is actuated concurrently with another ultrasonic emitter element, or each ultrasonic emitter element is actuated singly, and wherein the sound carrying wedge is adapted to couple to the area of interest;
    d. engaging the sound carrying wedge with the probe attached thereto over the wave coupling medium;
    e. transmitting a plurality of inspection signals to the area of interest by actuating the ultrasonic emitter array to provide the plurality of inspection signals, wherein the plurality of inspection signals is focused on a specific area and at a specific distance and further wherein the sound carrying wedge is adapted to receive the plurality of inspection signals and to disperse the plurality of inspection signals at a plurality of predetermined inspection signal angles into the area of interest;
    f. manipulating the probe along the area of interest while actuating the ultrasonic emitter to produce at least one detection signal, wherein the at least one detection signal is a reflected inspection signal;
    g. transmitting the at least one detection signal to a data storage in communication with a processor;
    h. using computer instructions stored in the data storage to present the at least one detection signal and a known reference level stored in the data storage to a user; and
    i. comparing the at least one detection signal to the known reference level to determine if the at least one detection signal is within a standard deviation of the known reference level.

2. The method of claim 1, further comprising:
    a. manipulating the probe along the area of interest while actuating the ultrasonic emitter to produce a plurality of detection signals;
    b. compiling the plurality of detection signals to determine any detection signals falling outside of the standard deviation of the known reference level; and
    c. presenting the compiled detection signals to the user for a quick determination of an area of interest with detection signals falling outside the standard deviation of the known reference level.

3. The method of claim 1, further comprising using additional sound carrying wedges, wherein each of the additional sound carrying wedges is adapted to disperse an additional plurality of inspection signals at additional predetermined inspection signal angles, and wherein each additional sound carrying wedge enables additional detection signals to be produced for the area of interest.

4. The method of claim 1, wherein the predetermined inspection signal angles range from zero degrees to ninety degrees.

5. The method of claim 1, further comprising providing communication between the data storage, the processor, or combinations thereof with a network, wherein a client device is in communication with the network for receiving inspection data from the data storage, the processor, or combinations thereof, enabling the user to remotely view the inspection data as an inspection occurs or as an inspection is completed.

6. The method of claim 5, wherein the client device is a mobile phone, a computer, a lap top, or a tablet.

7. The method of claim 1, further comprising adapting the sound carrying wedge to couple to the area of interest by:
    a. measuring a curvature of a surface of the area of interest; and
    b. shaping a sound carrying wedge that is not adapted to couple to the area of interest to have a curvature that matches the measured curvature of the surface of the area of interest.

8. The method of claim 1, wherein detection signals that fall outside of known reference levels indicate internal or external flaws of the down hole drilling system including: fractures, cracks, hairline cracks, rust, degradation, corrosion, residue build-up, other types of flaws found in the inherent, processing and service of the down hole drilling system, or combinations thereof.

9. The method of claim 1, wherein the down hole drilling system comprises: a drilling motor, drilling motor components, drilling tools, drilling tool components, a mud motor bottom hole assembly, cylindrical components of down hole tools, ball bearings, housings, threaded areas of the down hole drilling system, transition areas of the down hole drilling system, gap subs, or combinations thereof.

10. The method of claim 1, wherein the removing of particulate from the down hole drilling system comprises: using a mechanical grinder to remove the particulate, using a chemical to remove the particulate, using water to remove the particulate, using a hose with liquid to remove the particulate, using a pressure washer to remove the particulate, or combinations thereof.

11. The method of claim 1, further comprising using as the wave coupling medium an ultrasonic conductive gel, water, or combinations thereof.

12. The method of claim 1, wherein the probe is attached to the sound carrying wedge using nuts and bolts, screws, another fastening means, or combinations thereof.

13. The method of claim 1, wherein the probe further comprises a plurality of piezoelectric crystals.

14. The method of claim 1, wherein the sound carrying wedge is formed of ceramic, rexolite, or another material.

15. The method of claim 1, wherein the sound carrying wedge comprises a curved contact surface that is adapted to form-fittingly match a curvature of the area of interest, and wherein the curved contact surface is in full contact with the area of interest when the sound carrying wedge is engaged over the wave coupling medium.

16. The method of claim 1, further comprising using the probe to receive the at least one detection signal and to transmit the at least one detection signal to the data storage.

17. A method for inspecting down hole drilling systems for identifying indications of flaws in material, the method comprising:
   a. disposing a wave coupling medium on an area of interest of the down hole drilling system;
   b. attaching a probe to a sound carrying device, wherein the probe comprises an ultrasonic emitter array comprising a plurality of ultrasonic emitter elements configured to be independently actuated, wherein each ultrasonic emitter element is actuated concurrently with another ultrasonic emitter element, or each ultrasonic emitter element is actuated singly, and wherein the sound carrying wedge is adapted to form-fittingly couple to the area of interest;
   c. engaging the sound carrying wedge with the probe attached thereto over the wave coupling medium;
   d. transmitting multiple inspection signals from the probe, through the sound carrying wedge, through the wave coupling medium, and into the area of interest by actuating the ultrasonic emitter array, wherein each of the multiple inspection signals is focused on a specific area and at a specific distance, and further wherein each of the multiple inspection signals is transmitted at an angle into the area of interest;
   e. receiving at least one detection signal, wherein the at least one detection signal is an inspection signal reflected from the area of interest; and
   f. comparing the at least one detection signal to a known reference level to determine if the at least one detection signal is within a standard deviation of the known reference level.

18. The method of claim 17, further comprising removing particulate from the down hole drilling system before disposing the wave coupling medium on the area of interest of the down hole drilling system.

19. A method for inspecting down hole drilling systems for identifying indications of flaws in material, the method comprising:
   a. adapting a sound carrying wedge to form-fittingly couple to an area of interest of a down hole drilling system;
   b. disposing a wave coupling medium on the area of interest;
   c. attaching a probe to the sound carrying wedge wherein the probe comprises ultrasonic emitter array comprising a plurality of ultrasonic emitter elements configured to be independently actuated, and further wherein each ultrasonic emitter element is actuated concurrently with another ultrasonic emitter element, or each ultrasonic emitter element is actuated singly;
   d. engaging the sound carrying wedge with the probe attached thereto over the wave coupling medium;
   e. transmitting a plurality of inspection signals to the area of interest by actuating the probe, wherein the sound carrying wedge receives the plurality of inspection signals and disperses the plurality of inspection signals at a plurality of inspection signal angles into the area of interest, and further wherein the plurality of inspection signals is focused on a specific area and at a specific distance;
   f. receiving at least one detection signal, wherein the at least one detection signal is an inspection signal reflected from the area of interest; and
   g. comparing the at least one detection signal to a known reference level to determine if the at least one detection signal is within a standard deviation of the known reference level.

20. The method of claim 19, wherein adapting the sound carrying wedge to form-fittingly couple to the area of interest of the down hole drilling system comprises:
   a. measuring a curvature of a surface of the area of interest; and
   b. shaping a sound carrying wedge that is not adapted to couple to the area of interest to have a curvature that matches the measured curvature of the surface of the area of interest.

* * * * *